(12) United States Patent
Kurihara et al.

(10) Patent No.: US 11,090,201 B2
(45) Date of Patent: Aug. 17, 2021

(54) ABSORBENT ARTICLE

(71) Applicant: DAIO PAPER CORPORATION, Ehime (JP)

(72) Inventors: Ryoko Kurihara, Tochigi (JP); Junta Tagomori, Tochigi (JP); Mariko Nagashima, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 274 days.

(21) Appl. No.: 16/083,091

(22) PCT Filed: Mar. 24, 2017

(86) PCT No.: PCT/JP2017/012002
§ 371 (c)(1),
(2) Date: Sep. 7, 2018

(87) PCT Pub. No.: WO2017/164366
PCT Pub. Date: Sep. 28, 2017

(65) Prior Publication Data
US 2019/0053958 A1 Feb. 21, 2019

(30) Foreign Application Priority Data
Mar. 24, 2016 (JP) .............................. JP2016-060583

(51) Int. Cl.
*A61F 13/511* (2006.01)
*A61F 13/47* (2006.01)
(Continued)

(52) U.S. Cl.
CPC ........ *A61F 13/51104* (2013.01); *A61F 13/47* (2013.01); *A61F 13/511* (2013.01);
(Continued)

(58) Field of Classification Search
CPC ........ A61F 13/511–51394; A61F 2013/51178; A61F 13/51104; A61F 13/51108;
(Continued)

(56) References Cited

U.S. PATENT DOCUMENTS

| 4,668,230 A | 5/1987 | Damico et al. |
| 6,506,961 B1 * | 1/2003 | Levy .................. A61F 13/4756 |
| | | 604/380 |

(Continued)

FOREIGN PATENT DOCUMENTS

| JP | 61-92668 A | 5/1986 |
| JP | 2008-25083 A | 2/2008 |

(Continued)

OTHER PUBLICATIONS

International Search Report dated Jun. 20, 2017 of corresponding application No. PCT/JP2017/012002; 2 pgs.

*Primary Examiner* — Susan S Su
(74) *Attorney, Agent, or Firm* — Maier & Maier, PLLC

(57) ABSTRACT

An absorbent article that prevents back flow and that uses cotton fibers in the surface sheet. The absorbent article is an incontinence pad having at least a medium volume for absorbing at least 20 cc of urine. A surface sheet is formed by coating, with a water-repellent, a spunlace non-woven fabric comprising 100 wt % of cotton fibers. The skin-facing surface side is provided with: a plurality of protrusions that extend along the longitudinal direction of the incontinence pad and are formed with gaps therebetween in the widthwise direction; and a plurality of recesses that extend along the longitudinal direction of the incontinence pad and are formed between adjacent protrusions. The recesses are formed thinner than the protrusions. A plurality of openings, which penetrate the incontinence pad from the front to the (Continued)

rear thereof, is formed along the recesses in at least a section (H) corresponding to an excretory opening.

4 Claims, 6 Drawing Sheets

(51) Int. Cl.
  *A61F 13/513* (2006.01)
  *A61F 13/537* (2006.01)
  *A61L 15/34* (2006.01)
  *A61F 13/512* (2006.01)
  *A61F 13/53* (2006.01)

(52) U.S. Cl.
  CPC .......... *A61F 13/512* (2013.01); *A61F 13/513* (2013.01); *A61F 13/5116* (2013.01); *A61F 13/51108* (2013.01); *A61F 13/51113* (2013.01); *A61F 13/51121* (2013.01); *A61F 13/53* (2013.01); *A61F 13/537* (2013.01); *A61L 15/34* (2013.01); *A61F 2013/51178* (2013.01)

(58) Field of Classification Search
  CPC .............. A61F 13/512; A61F 13/51113; A61F 2013/51117; A61F 13/5116; A61F 2013/51165–51182
  USPC .................................................. 604/358–391
  See application file for complete search history.

(56) References Cited

U.S. PATENT DOCUMENTS

| | | | |
|---|---|---|---|
| 8,450,556 B2* | 5/2013 | Miyamoto | B32B 7/02 604/380 |
| 9,237,974 B2* | 1/2016 | Ohashi | A61F 13/53 |
| 10,322,037 B2* | 6/2019 | Noda | A61F 13/42 |
| 2004/0140047 A1* | 7/2004 | Sato | B32B 3/30 156/205 |
| 2004/0162536 A1* | 8/2004 | Becker | A61F 13/15203 604/367 |
| 2006/0247590 A1* | 11/2006 | Ito | A61F 13/474 604/379 |
| 2010/0178456 A1* | 7/2010 | Kuroda | B32B 7/04 428/136 |
| 2012/0226250 A1* | 9/2012 | Sato | A61F 13/51104 604/367 |
| 2013/0261585 A1* | 10/2013 | Lee | A61F 13/8405 604/385.01 |
| 2014/0039436 A1* | 2/2014 | Maranghi | A61F 13/4756 604/372 |

FOREIGN PATENT DOCUMENTS

| | | |
|---|---|---|
| JP | 2009-148328 A | 7/2009 |
| JP | 2010-269029 A | 12/2010 |
| JP | 2011-30940 A | 2/2011 |
| JP | 2011-174193 A | 9/2011 |
| JP | 2015-171649 A | 10/2015 |

* cited by examiner

[FIG. 1]
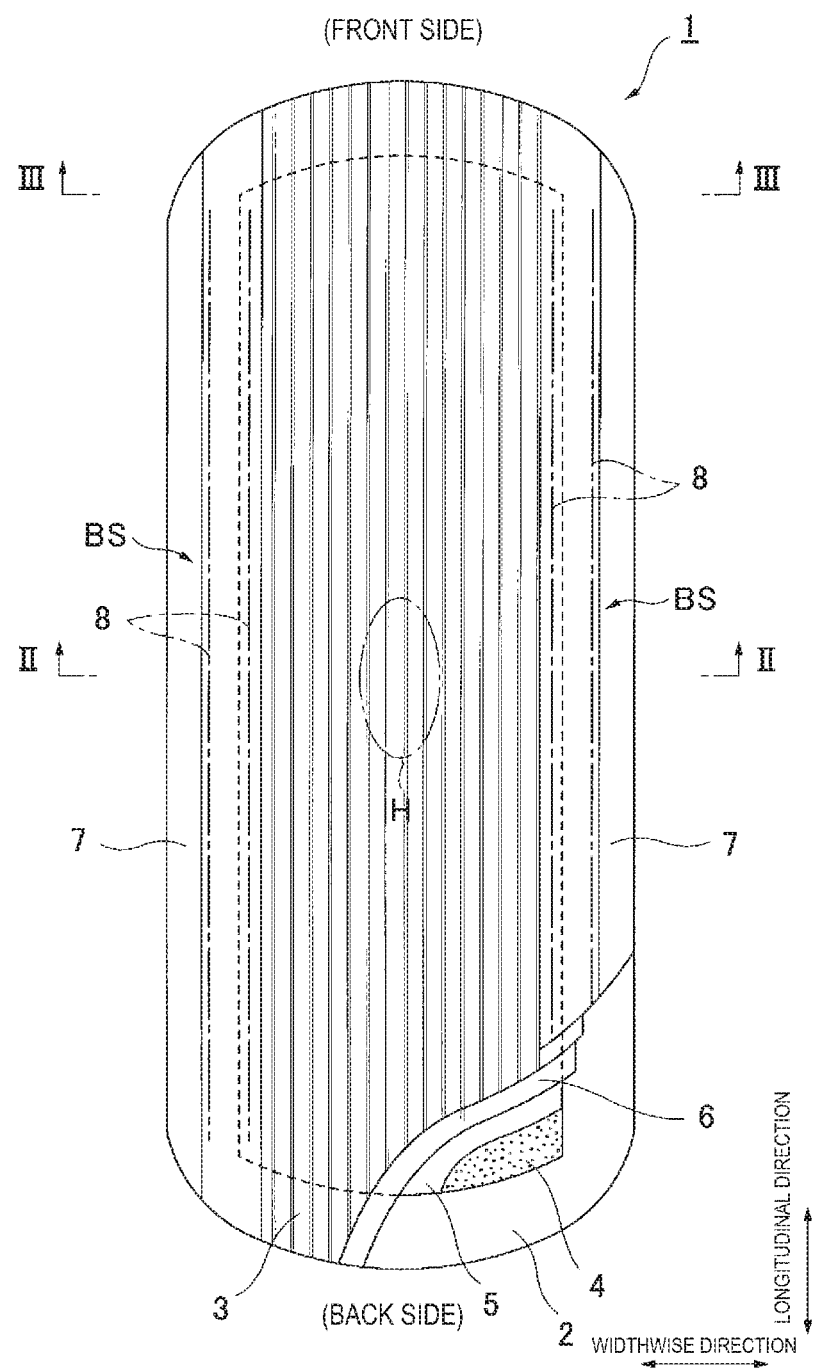

[FIG. 2]
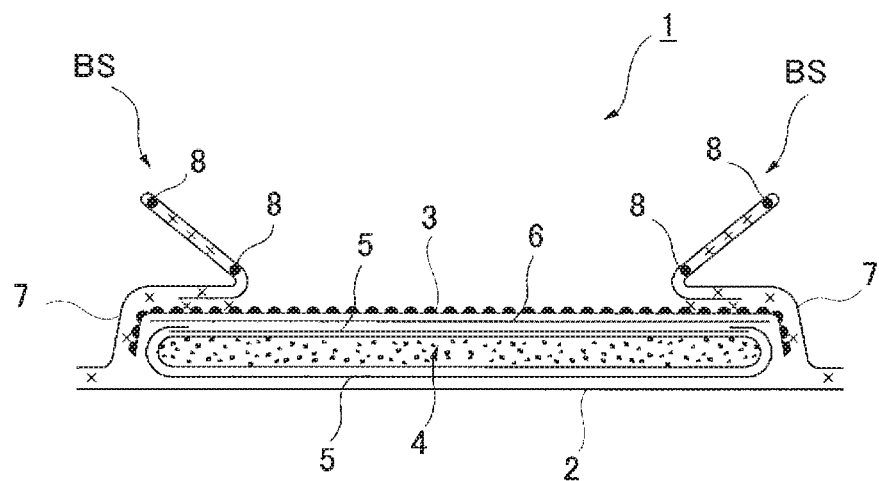
[FIG. 3]
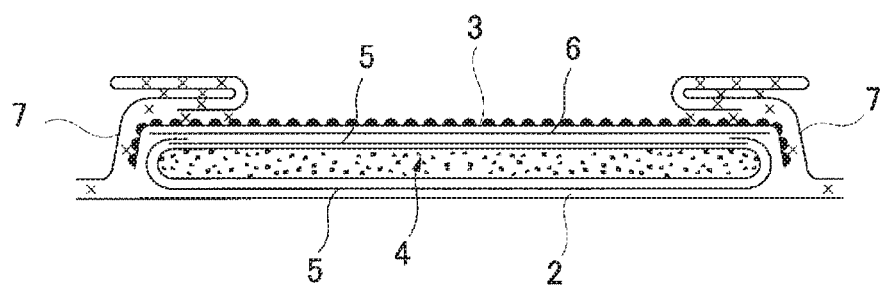

[FIG. 4]
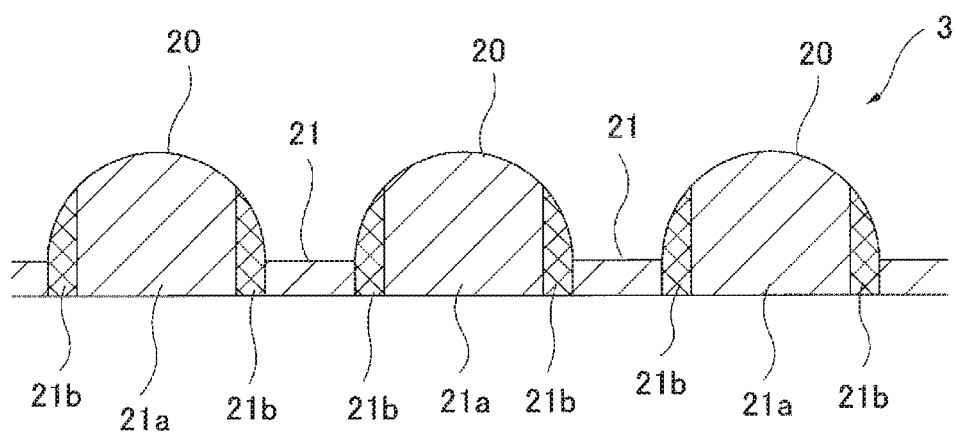
[FIG. 5]
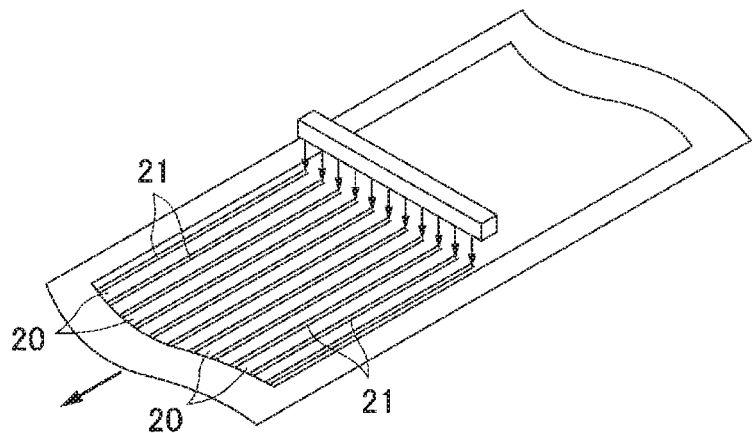

[FIG. 6]
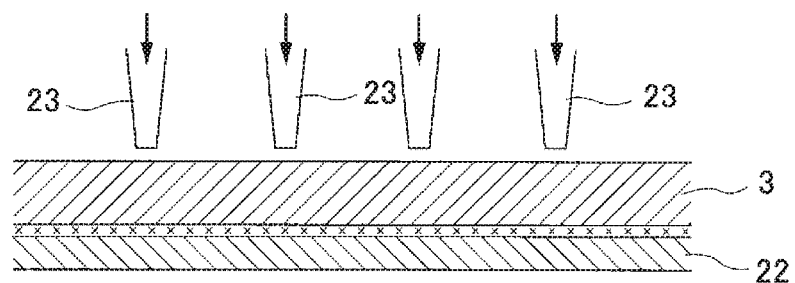
[FIG. 7]
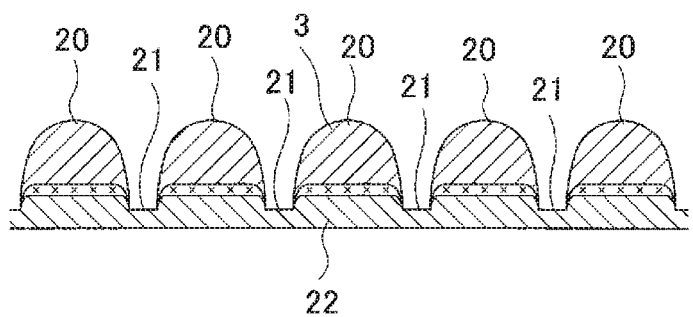

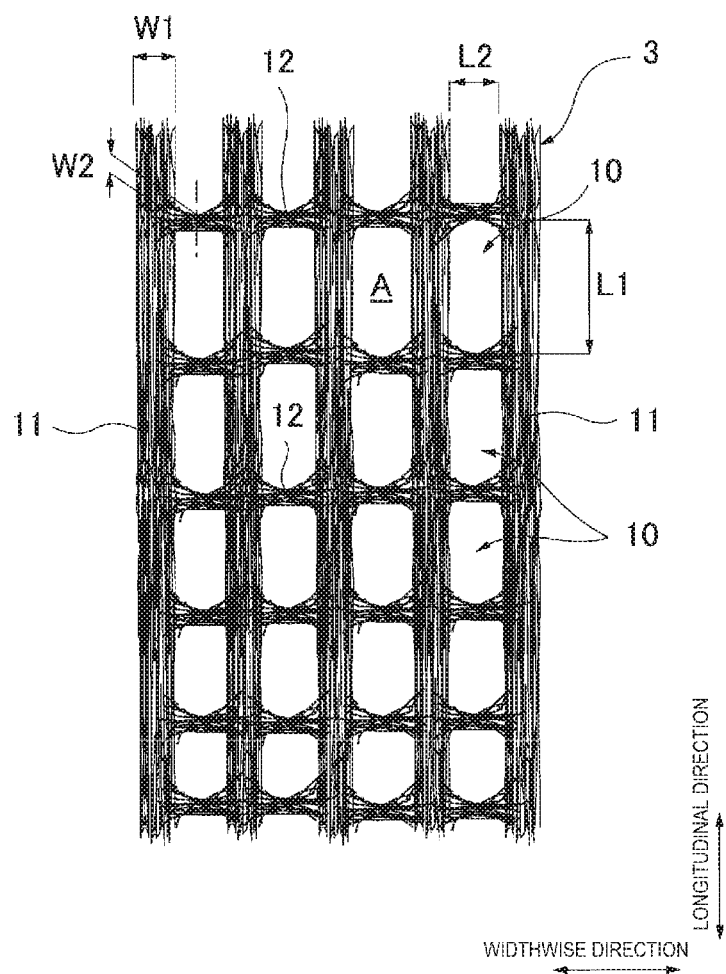
[FIG. 8]

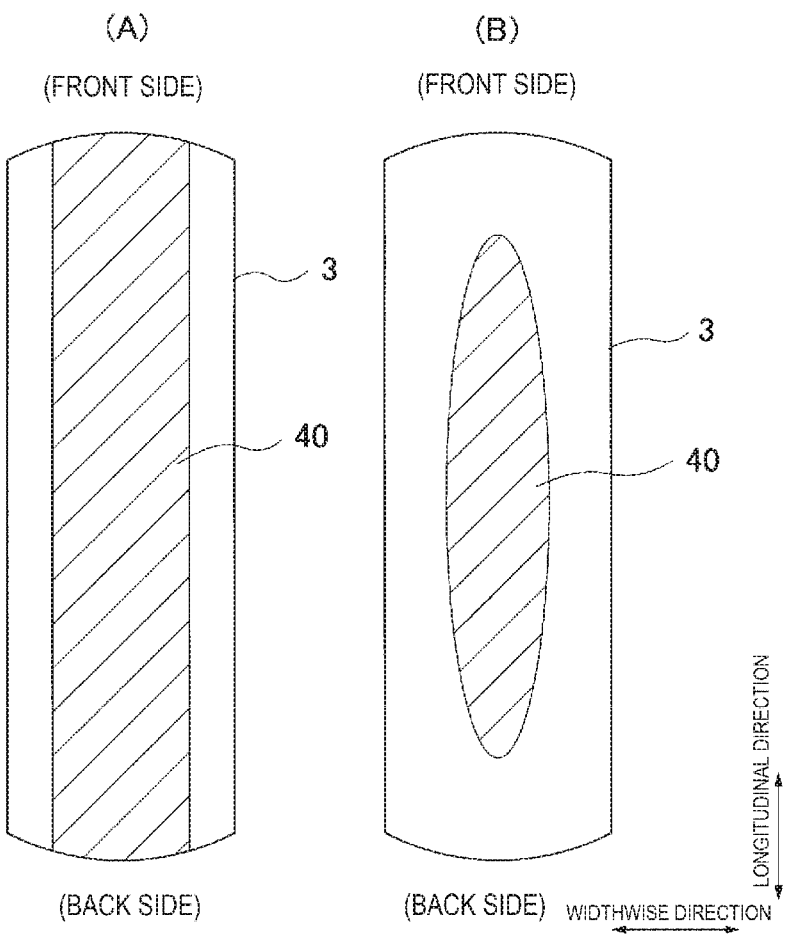

ABSORBENT ARTICLE

FIELD

The present invention relates to an absorbent article mainly used for an incontinence pad, and particularly relates to an absorbent article in which a surface sheet includes 100 wt % of cotton fiber and unevenness is formed on a skin-facing surface side.

BACKGROUND

Conventionally, an absorbent article in which an absorber made of paper cotton such as pulverized pulp is interposed between a surface sheet and a liquid impermeable back sheet such as a polyethylene sheet or a polyethylene sheet laminated non-woven fabric has been known as an absorbent article for women such as an incontinence pad, a panty liner (Pantyliner), or a sanitary napkin.

The surface sheet forms a skin-contact surface, and thus is required to be flexible, obtain a dry feel even after absorption of an excreted liquid, and cause little irritation to a skin. As a material satisfying such requirements, a non-woven fabric of synthetic fibers and a resin mesh sheet have been widely adopted in a field of absorbent articles, particularly in a field of incontinence pads. However, there has been a problem that a surface sheet made of a synthetic fiber causes itching, rash, etc.

As a solution to this problem, a surface sheet made of cotton fiber (cotton) has been proposed. However, in an absorbent article, a surface sheet has high liquid permeability, and it is desired that a liquid be allowed to rapidly reach an absorber. However, when an ordinary absorbent cotton fiber is contained in the surface sheet, there is a problem that the surface sheet has a high liquid retaining property and a sticky feeling tends to remain on the surface.

In addition, while the absorbent article in which the surface sheet is made of cotton fiber has an advantage that a soft tactile property can be realized as in underwear, the absorbent article has a high liquid retaining property as described above. Thus, when a large amount of body fluid is discharged, the body liquid remains on the surface sheet and causes stuffiness, rash, etc. due to wearing for a long time. For this reason, in a conventional absorbent article, using cotton fiber as a surface sheet is limited to a product that requires less absorption of a body fluid such as a panty liner.

Examples of such an absorbent article in which cotton fiber is used for a surface sheet may include Patent Documents 1 and 2, etc. Patent Document 1 discloses an absorbent article in which a surface sheet includes a cotton non-woven fabric, a heat-fusible fiber sheet having a lower fiber density than that of the cotton non-woven fabric and having hydrophilicity is located below the surface sheet and interposed between the surface sheet and an absorber, and embossment is performed a plurality of times from a surface side in these laminated states.

In addition, Patent Document 2 discloses an absorbent article in which a topsheet is obtained by applying a water repellent to a spunlace non-woven fabric including 40 to 100 wt % of cotton fiber and 60 to 0 wt % of synthetic fiber and setting water absorbency of a skin-contact surface to 0 mm to 5 mm, and at least an excretory opening part has a plurality of openings penetrating therethrough from a front to a rear thereof. According to such an absorbent article, a lot of benefits of cotton fiber such as excellent skin contact and hardly causing itching or rash are provided by adopting the spunlace non-woven fabric having high cotton fiber content as the topsheet. Moreover, a residual liquid on the surface which becomes a problem at this time is sufficiently improved by applying (externally adding) the water repellent to ensure sufficiently low water absorbency of the skin-contact surface. However, when the water absorbency is merely lowered, a liquid component of excrement hardly permeates the topsheet, and lateral leakage, etc. is caused. Thus, in the absorbent article described in Patent Document 1, rapid liquid absorption is made possible by providing at least the excretory opening part in the topsheet with the plurality of openings penetrating therethrough from the front to the rear. As a result, Patent Document 1 describes effects that stickiness due to residual liquid on the surface can be sufficiently prevented and that the absorbed excreted liquid hardly returns to the surface side of the topsheet due to water repellency of the topsheet.

CITATION LIST

Patent Document

Patent Document 1: JP-A-2009-148328
Patent Document 2: JP-A-2010-269029

SUMMARY

However, in a case of absorbing a medium volume or more of urine corresponding to a total urine volume of 20 cc, there is concern that water may be retained in the surface sheet in the absorbent articles described in Patent Documents 1 and 2, and there is a need for a scheme of not retaining water in the surface sheet as much as possible.

In addition, the absorbent article is formed in a shape which is long in a longitudinal direction and has a narrow width, and thus is required to prevent lateral leakage by promoting diffusion of urine in the longitudinal direction of the absorbent article.

Further, in Patent Documents 1 and 2, since the skin-contact surface of the surface sheet is formed substantially flat, when cotton fiber is used as the surface sheet, a sticky feeling is easily felt due to water retention of the surface sheet, itching, rash, etc. are caused, and a sufficient cushioning characteristic is not obtained.

In this regard, a principal object of the invention is to provide an absorbent article using cotton fiber as a surface sheet, which reduces water retention of the surface sheet as much as possible, easily diffuses liquid in a longitudinal direction, and is excellent in a cushioning characteristic.

As the invention according to claim 1 for solving the above-mentioned problems, provided is an absorbent article in which an absorber is interposed between a surface sheet and a back sheet, wherein the absorbent article is an incontinence pad having a medium volume or more for absorbing 20 cc or more of urine, and the surface sheet is formed by applying a water repellent to a spunlace non-woven fabric containing 100 wt % of cotton fiber, a plurality of protrusions formed along a longitudinal direction of the absorbent article and at an interval in a widthwise direction and a plurality of recesses formed along the longitudinal direction of the absorbent article and between adjacent protrusions are provided on a side of a skin-facing surface, the recesses are formed thinner than the protrusions, and a plurality of openings penetrating the incontinence pad from a front to a rear thereof is formed along the recesses at least in a section corresponding to an excretory opening.

The invention described in claim 1 is targeted for an incontinence pad which absorbs urine caused by abdominal pressure incontinence instantaneously discharged when a force is applied to an abdomen, for example, at the time of sneezing, coughing, lifting a heavy object, etc. or urine caused by impending incontinence instantaneously discharged when an intense micturition desire is rapidly felt and may not be tolerated, and has a medium volume or more for absorbing 20 cc or more of a total urine volume. In the case of the incontinence pad, the incontinence pad is continuously used until the second incontinence in many cases, and the incontinence pad is worn for a long time in a state after the first incontinence and discharged after subsequent urination in many cases.

In addition, in the absorbent article, a material obtained by applying a water repellent to a spunlace non-woven fabric containing 100 wt % of cotton fiber and provided with a plurality of protrusions formed along a longitudinal direction of the absorbent article and at an interval in a widthwise direction and a plurality of recesses formed along the longitudinal direction of the absorbent article and between adjacent protrusions on a side of a skin-facing surface is used as the surface sheet. For this reason, by adopting the spunlace non-woven fabric made of 100 wt % of cotton fiber, a soft tactile property is obtained, and skin trouble during wearing such as itching or rash may be allowed to rarely occur even after wearing for a long time. Water retention of the surface sheet which is a problem at this time is solved by applying the water repellent and forming unevenness along the longitudinal direction of the absorbent article on the skin-facing surface side to promote vertical diffusion of the excreted liquid, thereby reducing the amount of the excreted liquid permeating per unit area.

In addition, in the surface sheet, since the recesses are formed thinner than the protrusions, a liquid flowing along the recesses easily moves to the absorber side on a lower layer through the recesses. Further, since the plurality of openings penetrating the incontinence pad from the front to the rear thereof is formed along the recesses at least in the section corresponding to the excretory opening of the surface sheet, urine passing through the openings easily passes through the surface sheet, and the amount of water retention of the surface sheet is reduced.

Further, since the skin-facing surface side of the surface sheet is formed in an uneven shape, a compressive restoring force of the surface sheet is increased, a cushioning characteristic is improved, and the uneven shape on the skin-facing surface side is easily maintained.

As the invention according to claim 2, provided is the absorbent article according to claim 1, wherein the surface sheet is formed such that a basis weight of the recesses is lower than an average basis weight of the protrusions and a density of the recesses is lower than an average density of the protrusions.

In the invention described in claim 2, a material formed such that a basis weight of the recesses is lower than an average basis weight of the protrusions and a density of the recesses is lower than a density of the protrusions is used as the surface sheet. To manufacture such a surface sheet, an airflow jetted from a plurality of nozzles disposed at a predetermined interval is sprayed onto a surface of the sheet-shaped cotton non-woven fabric whose surface is flat. In this way, a part of cotton fiber in a portion onto which the airflow is blown moves to both sides to form the recesses, the protrusions are formed between adjacent recesses, and the protrusions and the recesses have a predetermined basis weight and density relationship.

As the invention according to claim 3, provided is the absorbent article according to claim 1, wherein a second sheet made of thermoplastic fiber is attached to a side of the absorber of the surface sheet, the surface sheet and the second sheet are joined by heat sealing of the second sheet in the recesses, a basis weight of the recesses is substantially the same as a basis weight of the protrusions, and a density of the recesses is higher than a density of the protrusions.

In the invention described in claim 3, the second sheet made of thermoplastic fiber is attached to the absorber side of the surface sheet, and the surface sheet and the second sheet are joined by heat sealing of the second sheet in the recesses by compression from the surface side of the surface sheet. Since the surface sheet is made of cotton fiber, a shape of a recessed groove by compression is hardly preserved. However, molten thermoplastic fiber penetrates into the surface sheet and fuses by compression together with the second sheet made of thermoplastic fiber, and thus a state in which the surface sheet is compressed is maintained. In this way, the basis weight of the recesses is substantially the same as the basis weight of the protrusions, and the density of the recesses is higher than the density of the protrusions. For this reason, a body fluid absorbed in the surface sheet is drawn to the recesses having high density from the protrusions having low density due to a capillary action caused by density gradient of the fiber, liquid transfer from the recesses to the absorber side is promoted, and the amount of water retention of the protrusions in contact with the skin surface decreases.

As the invention according to claim 4, provided is the absorbent article according to any one of claims 1 to 3, wherein glyceryl stearate is used as the water repellent.

In the invention described in claim 4, by using glyceryl stearate as the water repellent, urine is not absorbed by cotton fiber of the surface sheet and easily flows to the absorber side.

As the invention according to claim 5, provided is the absorbent article according to any one of claims 1 to 4, wherein the surface sheet is made of absorbent cotton fiber or non-absorbent cotton fiber.

In the invention described in claim 5, as the surface sheet, absorbent cotton fiber may be used, or non-absorbent cotton fiber may be used. When non-absorbent cotton fiber is used, the amount of water retention of the surface sheet may be further reduced, and thus residual liquid of the surface sheet is rarely generated.

As described above, according to the invention, in an absorbent article using cotton fiber as a surface sheet, water retention of the surface sheet may be reduced as much as possible, liquid easily diffuses in a longitudinal direction, and a cushioning characteristic is excellent.

BRIEF DESCRIPTION OF THE DRAWINGS

FIG. 1 is a partially cutaway development view of an incontinence pad 1 according to the invention.

FIG. 2 is an arrow view taken along line II-II of FIG. 1.

FIG. 3 is an arrow view taken along line III-III of FIG. 1.

FIG. 4 is an enlarged cross-sectional view of a surface sheet 3.

FIG. 5 is a perspective view illustrating a manufacturing apparatus according to a first manufacturing method of the surface sheet 3.

FIG. 6 is a cross-sectional view illustrating a manufacturing procedure according to a second manufacturing method of the surface sheet 3.

FIG. 7 is an enlarged cross-sectional view of the surface sheet 3 manufactured by the second manufacturing method.

FIG. 8 is an enlarged plan view of a case in which an opening is formed in the surface sheet 3.

FIG. 9 is a development view illustrating a water repellent application pattern on a surface of the surface sheet 3.

DETAILED DESCRIPTION

Hereinafter, embodiments of the invention will be described in detail with reference to drawings. The invention is an incontinence pad 1 for medium volume or more suitable for absorbing total urine volume of 20 cc or more, and is particularly suitable to absorb urine caused by abdominal pressure incontinence instantaneously discharged when a force is applied to an abdomen, for example, at the time of sneezing, coughing, lifting a heavy object, etc. or urine caused by impending incontinence instantaneously discharged when an intense micturition desire is rapidly felt and may not be tolerated.

One Example of Basic Structure of Incontinence Pad

As illustrated in FIG. 1 to FIG. 3, the incontinence pad 1 according to the invention mainly includes a liquid impermeable back sheet 2 made of a polyethylene sheet, etc., a surface sheet 3 forming a skin-contact surface and allowing rapid permeation of urine, etc., an absorber 4 made of cotton-like pulp, synthetic pulp, etc. and interposed between both the sheets 2 and 3, and a pair of left and right three-dimensional gathers BS and BS which uses substantially side edge portions of the absorber 4 as standing bases and is provided to protrude to a skin side within a predetermined section in a front-back direction to include at least an ureteral opening H of a wearer. Around the absorber 4, at upper and lower end edge portions thereof, the liquid impermeable back sheet 2 and an outer edge portion of the surface sheet 3 are joined by an adhesive such as a hot melt or adhesive means such as heat sealing. In addition, at both the side edge portions thereof, the liquid impermeable back sheet 2 laterally extending beyond the absorber 4 and side non-woven fabrics 7 forming the three-dimensional gathers BS are joined by an adhesive such as a hot melt or adhesive means such as heat sealing. In the illustrated example, the absorber 4 has a single-layer structure. However, it is possible to adopt a multi-layer structure forming a middle-high portion or a multi-layer structure in which absorbers having the same size and shape are stacked.

As the liquid impermeable back sheet 2, a sheet material having at least a water-blocking property such as polyethylene has been used. However, in recent years, a sheet material having moisture permeability tends to be used from a viewpoint of preventing stuffiness. A microporous sheet obtained by melt-kneading an inorganic filler in an olefin-based resin such as polyethylene or polypropylene to mold a sheet, and then stretching the sheet in a uniaxial direction or biaxial direction is suitably used as this sheet material having the water-blocking property and the moisture permeability. One or a plurality of adhesive layers (not illustrated) is formed on a non-use surface side (outer surface) of the liquid impermeable back sheet 2, and the incontinence pad 1 is fixed to the underwear at the time of wearing on a body. A poly-laminate non-woven fabric in which a plastic film and a non-woven fabric are laminated may be used as the liquid impermeable back sheet 2.

In the illustrated example, a width of the surface sheet 3 is slightly wider than a width of the absorber 4 and merely covers the absorber 4, and an outer side of the surface sheet 3 in a widthwise direction is covered by the side non-woven fabrics 7 (a member different from the surface sheet 3) extending from both side surfaces of the surface sheet 3. A central part of each of the side non-woven fabrics 7 in the widthwise direction forms each of the three-dimensional gathers BS. As the side non-woven fabric 7, it is possible to use a non-woven fabric material subjected to an appropriate water-repellent treatment or hydrophilic treatment depending on the purpose of preventing penetration of urine, etc. or enhancing feeling of touch. As the side non-woven fabric 7, it is possible to use a fabric formed by an appropriate processing method using natural fiber, synthetic fiber, regenerated fiber, etc. as a material, and it is preferable to a non-woven fabric having a suppressed basis weight and air permeability to eliminate a stiff feeling and prevent stuffiness. Specifically, it is desirable to use a non-woven fabric manufactured by setting a basis weight to 15 to 23 g/m$^2$, and a water-repellent treated non-woven fabric coated with a silicon-based or paraffin-based water repellent, etc. to surely prevent permeation of a body fluid is suitably used.

As illustrated in FIG. 2 and FIG. 3, in the side non-woven fabric 7, an outer part of a middle portion in the widthwise direction is bonded by an adhesive such as a hot melt over a range from an inner position of the absorber 4 to an outer edge of the liquid impermeable back sheet 2 slightly beyond a side edge of the absorber.

Meanwhile, an inner side portion of the side non-woven fabric 7 is substantially doubly folded back. Further, inside this double sheet, in a middle part in a height direction thereof, one or a plurality of (two in the illustrated example) threadlike elastically stretchable members 8 and 8 fixed at both ends or an appropriate position in the longitudinal direction are arranged in a state in which the both ends or the appropriate position in the longitudinal direction is fixed. As illustrated in FIG. 3, this double sheet part is fixed to the surface sheet 3 side in a folded state at front and rear end portions.

<Surface Sheet>

The surface sheet 3 forms the skin-contact surface which is a part covering a skin side of the absorber 4, and is characterized by including a spunlace non-woven fabric made of 100 wt % of cotton fiber. The spunlace non-woven fabric has advantages that an adhesive is not used and the spunlace non-woven fabric has flexibility.

The non-woven fabric of the surface sheet 3 uses cotton fiber alone and does not contain synthetic fiber. As the cotton fiber, it is possible to use various cotton fibers such as raw cotton of a cotton plant, refined/bleached cotton fiber, cotton fiber dyed after being refined/bleached, refined/bleached absorbent cotton fiber, and recovered wool obtained by defibrating yarn or fabric, and it is particularly preferable to use non-absorbent cotton slightly having water repellency even in a fiber state due to natural fat and oil of cotton wax attached to a surface of cotton fiber.

In the surface sheet 3, as illustrated in FIG. 4, a plurality of protrusions 20, 20, . . . formed along the longitudinal direction of the incontinence pad 1 and at an interval in the widthwise direction and a plurality of recesses 21, 21, formed along the longitudinal direction of the incontinence pad 1 and between adjacent protrusions 20 and 20 are provided on the skin-facing surface side. Meanwhile, a non-skin-facing surface side (absorber 4 side) is formed substantially flat, almost the entire surface thereof is in contact with members arranged on the absorber 4 side, and the body fluid absorbed in the surface sheet 3 is easily transferred to the absorber 4.

In the example illustrated in FIG. 4, a cross-sectional shape of the protrusion 20 is formed in a semicircular dome shape. However, it is possible to adopt an arbitrary shape such as a quadrangular shape, a triangular shape, or a trapezoidal shape. In addition, a cross-sectional shape of the recess 21 is similarly arbitrary, and it is possible to adopt a U-shape, a V-shape, etc. in addition to a shape in which a bottom surface corresponds to a straight line as in the illustrated example.

A boundary between the protrusion 20 and the recess 21 disposed adjacent to each other may not be clear. For example, a portion protruding to the skin side from the recess 21 may be set as the protrusion 20. When the cross-sectional shape is formed in a continuous curved shape in which a curve bulging to the skin side from the protrusion 20 to the recess 21 and a curve bulging to a non-skin side are combined, a portion on the skin side of an inflection point of these curves may be set as the protrusion 20, and a portion on the non-skin side thereof may be set as the recess 21.

In the surface sheet 3, a thickness of the recess 21 is smaller than that of the protrusion 20. The thickness of the protrusion 20 refers to a distance in the thickness direction of the surface sheet between a top portion of the protrusion 20 on the skin-facing surface side and the outer surface on the non-skin-facing surface, and the thickness of the recess 21 refers to a distance in the thickness direction of the surface sheet between a bottom portion of the recess 21 on the skin-facing surface side and the outer surface on the non-skin-facing surface. The thickness of the protrusion 20 is set to 0.25 to 2 mm, preferably 0.3 to 0.8 mm, and the thickness of the recess 21 is set to 0.1 to 0.5 mm, preferably 0.15 to 0.3 mm. The thickness is determined according to JIS-L 1913.

A sheet obtained by applying the water repellent to the spunlace non-woven fabric made of 100 wt % of cotton fiber and providing the plurality of protrusions 20, 20, ... formed along the longitudinal direction of the incontinence pad 1 and at the interval in the widthwise direction and the plurality of recesses 21, 21, ... formed along the longitudinal direction of the incontinence pad 1 and between the adjacent protrusions 20 and 20 on the skin-facing surface side is used as the surface sheet 3. Thus, by adopting the spunlace non-woven fabric made of 100 wt % of cotton fiber, a soft tactile property is obtained, and skin trouble during wearing such as itching or rash may be allowed to rarely occur even after wearing for a long time. Water retention of the surface sheet 3 which is a problem at this time is solved by forming unevenness along the longitudinal direction of the incontinence pad 1 on the skin-facing surface side of the surface sheet 3 to promote vertical diffusion of the excreted liquid along the recess 21, thereby reducing the amount of the excreted liquid permeating per unit area. Specifically, since unevenness is formed along the longitudinal direction of the incontinence pad 1 on the skin-facing surface side of the surface sheet 3, the excreted liquid easily diffuses in the longitudinal direction of the incontinence pad 1 along the recess 21. Since the amount of the excreted liquid permeating per unit area of the surface sheet 3 decreases when the excreted liquid diffuses over a wide range of the surface sheet 3, the amount of water retention of the surface sheet 3 may be reduced.

In addition, in the surface sheet 3, the recess 21 is formed to be thinner in thickness than the protrusion 20, and thus a liquid flowing along the recess 21 easily moves to a lower layer side through the recess 21. For this reason, the amount of water retention of the surface sheet 3 decreases.

Further, since the skin-facing surface side of the surface sheet 3 is formed in an uneven shape, a compressive restoring force of the surface sheet 3 is increased, a cushioning characteristic is improved, and the uneven shape on the skin-facing surface side is easily maintained.

It is desirable that an average basis weight of the entire surface sheet 3 is set to 20 to 40 $g/m^2$, preferably 27 to 34 $g/m^2$, more preferably 29 to 32 $g/m^2$. The basis weight is calculated by measuring a weight of 5 cm×30 cm×10 sheets using an electronic balance and performing square meter conversion.

Any one of two methods below may be used to manufacture the surface sheet 3 having the uneven shape. As a first method, as illustrated in FIG. 5, a sheet-shaped cotton non-woven fabric having a flat surface made of cotton fiber is placed on a mesh-shaped conveyor which moves in a certain direction and is provided with a plurality of vent holes having sizes that allow air to pass therethrough and do not allow the cotton fiber to pass therethrough, and a fluid such as air (hot air) is continuously ejected from a plurality of nozzles disposed at a predetermined interval in a direction orthogonal to a moving direction and blown onto the surface of the cotton non-woven fabric. In this way, as illustrated in FIG. 4, a part of fiber moves to both sides and the relatively depressed recess 21 is formed in a portion onto which the fluid is blown, and the relatively protruding protrusion 20 is formed in a portion therebetween onto which the fluid is not blown.

In the surface sheet 3 manufactured by this method, since fiber of the recess 21 moves to both side portions 20b of the protrusion 20 due to blowing of the fluid, a basis weight of the recesses 21 is lower than an average basis weight of the protrusions 20, and the density of the recesses 21 is lower than the average density of the protrusions 20. The basis weight and the density of the recesses 21 refer to the basis weight and the density of the surface sheet 3 present at a bottom of the recesses 21.

More specifically, in the protrusion 20, the density of the both side portions 20b of the protrusion 20 is higher than the density of a central portion 20a including the top portion of the protrusion 20. For this reason, the body fluid absorbed in the central portion 20a of the protrusion 20 is drawn to the both side portions 20b of the protrusion 20 having high density due to a capillary action caused by a density gradient of the fiber, the amount of water retention of the central portion 20a of the protrusion 20 in direct contact with the skin surface during wearing decreases, and a sticky feeling hardly occurs.

It is desirable that the average density of the protrusions 20 is set to 0.002 to 0.30 $g/cm^3$, preferably 0.002 to 0.20 $g/cm^3$, and it is desirable that the density of the recesses 21 is set to 0.001 to 0.20 $g/cm^3$, preferably 0.001 to 0.15 $g/cm^3$. In addition, it is desirable that the density of the central portion 10a of the protrusion 20 is set to 0.001 to 0.20 $g/cm^3$, preferably 0.001 to 0.15 $g/cm^3$, and it is desirable that the density of the both side portions 20b is set to 0.005 to 0.40 $g/cm^3$, preferably 0.01 to 0.50 $g/cm^3$.

It is desirable that the average basis weight of the protrusions 20 is set to 20 to 75 $g/m^2$, preferably 25 to 70 $g/m^2$, and it is desirable that the basis weight of the recesses 21 is set to 5 to 40 $g/m^2$, preferably 5 to 20 $g/m^2$. In addition, it is desirable that the basis weight of the central portion 10a of the protrusion 20 is set to 15 to 70 $g/m^2$, preferably 15 to 50 g/m², and it is desirable that the basis weight of the both side portions 20b is set to 20 to 120 g/m², preferably 25 to 90 g/m².

The basis weight and density of the protrusions 20 and the recesses 21 can be adjusted by changing a flow velocity or a flow rate of the fluid blown onto the cotton non-woven fabric at the time of forming unevenness on the surface sheet 3.

In addition, in the present manufacturing method, a plurality of openings may be provided at equal intervals along the recess 21 of the surface sheet 3 by intermittently providing a plurality of closing portions that closes the vent holes at equal intervals along a moving direction in a portion of the mesh-shaped conveyor onto which the fluid is blown. In the closing portion, since the blown fluid may not pass through the conveyor and changes to a flow in a direction along a plane direction of the conveyor, when fiber of the cotton non-woven fabric moves to be pushed away to the surroundings, a plurality of openings is formed at equal intervals along the recess 21 of the surface sheet 3 in which the closing portions are provided.

As a modification of the first manufacturing method, unevenness may be provided during hydroentanglement in a manufacturing process of the surface sheet 3 made of spunlace non-woven fabric. That is, simultaneously with entangling fibers with each other to form a sheet by depositing a web on an uneven net to spray a high-pressure water stream, the protrusion 20 is formed in a portion in which a depth of the net is deep, and the recess 21 is formed in a portion in which the depth is shallow.

Next, as a second method of manufacturing the uneven surface sheet 3, as illustrated in FIG. 6, a second sheet 22 made of thermoplastic fiber is attached to one surface side (surface side facing the absorber 4 of the surface sheet 3 (non-skin-facing surface side)) of a sheet-shaped cotton non-woven fabric having a flat surface made of cotton fiber using a hot melt adhesive, etc., and this laminated sheet is passed between an embossing roll including a plurality of embossed protrusions 23, 23, protruding outside on a circumferential surface and an anvil roll having a flat surface, thereby providing compressed grooves from the surface side of the cotton non-woven fabric. At the same time, the cotton non-woven fabric and the second sheet 22 are joined by heat sealing of the second sheet 22, thereby manufacturing the surface sheet 3 having an uneven surface as illustrated in FIG. 7.

The surface sheet 3 manufactured by this method is formed such that the basis weight of the recesses 21 is substantially the same as the basis weight of the protrusions 20, and the density of the recesses 21 is higher than the density of the protrusions 20. For this reason, the body fluid absorbed in the protrusion 20 is drawn to the recess 21 having high fiber density due to a capillary action caused by density gradient of the fiber, the amount of water retention of the protrusion 20 in contact with the skin surface decreases, and a sticky feeling hardly occurs.

It is desirable that a basis weight of the surface sheet 3 at this time is set to the above-mentioned average basis weight 20 to 40 g/m², preferably 27 to 34 g/m², more preferably 29 to 32 g/m².

In addition, it is desirable that the density of the protrusions 10 is set to 0.001 to 0.30 g/cm³, preferably 0.002 to 0.20 g/cm³, and it is desirable that the density of the recesses 21 is set to 0.01 to 3.0 g/cm³, preferably 0.01 to 1.0 g/cm³.

In the present manufacturing method, the compressed grooves provided on the surface sheet 3 may be set to continuous compressed grooves over the entire length of the incontinence pad 1 or set to intermittent compressed grooves in which a compressed portion and a non-compressed portion are alternatively provided along the longitudinal direction of the incontinence pad 1.

In the present manufacturing method, as the second sheet 22 joined to the surface sheet 3, it is preferable to use a sheet having a basis weight of about 10 to 200 g/m², preferably about 20 to 100 g/m² to impart a fluffy feeling and a cushion feeling to the surface sheet 3. As a material of the second sheet 22, a material having thermoplasticity may be used, and a material having hydrophilicity is particularly preferable. When the second sheet 22 having thermoplasticity and hydrophilicity is combined with the water repellent opening surface sheet 3 of the invention, unevenness of the surface sheet 3 is maintained, and a liquid pervious property and a back flow preventing property of the surface sheet 3 are improved. As such a material, it is possible to use a fiber obtained by performing a surface treatment using a hydrophilizing agent on a synthetic fiber such as an olefin-based fiber such as polyethylene or polypropylene, a polyester-based fiber, a polyamide-based fiber or a composite fiber, a copolymer, or a blend thereof, and imparting hydrophilicity thereto. Preferably, a fiber obtained by mixing polyethylene and polypropylene is used. As a fiber contained in the non-woven fabric, it is possible to use a long fiber, a short fiber, or a mixture thereof. It is desirable that the fineness is set to about 2.0 to 7.0 dtex, preferably about 4.0 to 6.0 dtex. As the second sheet 22, any known non-woven fabric such as an air-through, air laid, or spunbond non-woven fabric may be used, and it is preferable to use the air-through non-woven fabric which does not lower air permeability.

An uneven region formed by the protrusion 20 and the recess 21 is preferably formed on the entire surface of the surface sheet 3, and may be formed along the longitudinal direction in a central region part in the widthwise direction or partially formed in a circular or elliptical region including an excretory part.

In the surface sheet 3, as illustrated in FIG. 8, it is preferable to provide a plurality of openings 10, 10, . . . penetrating therethrough from the front to the rear along the recess 21 at least in a section H corresponding to the excretory opening to enhance liquid permeability. Specifically, the opening 10 may be formed by supporting a fiber material on a mesh-like support in a hydroentanglement process at the time of manufacturing spunlace. In this case, by changing a condition of the mesh to be used, it is possible to adjust a size of each opening and an opening ratio. The openings may be formed by performing punching (die cutting) on a non-woven fabric after manufacture. The opening 10 may be provided on the entire surface sheet, and is preferably provided at least in the section H corresponding to the excretory opening. Preferably, the opening 10 is provided in a region of 15% or more of the absorber length in a product length direction and 50% or more of the absorber width in a product widthwise direction including the section H corresponding to the excretory opening, more preferably in a region of 50% or more of the absorber length in the product length direction and 70% or more of the absorber width in the product widthwise direction including the section H corresponding to the excretory opening. When the formation region of the openings is less than 15% of the absorber length in the product length direction and less than 50% of the absorber width in the product widthwise direction, an incontinence range may not be covered, urine remains on the surface sheet 3, a sticky feeling is felt, and skin trouble such as itching or rash easily occurs at the time of wearing.

When a sheet in which the plurality of openings 10, 10, . . . penetrating therethrough from the front to the rear is formed at least in the section H corresponding to the excretory opening is used as the surface sheet 3, the body fluid rapidly permeates the surface sheet through the opening 10, and a problem that liquid remains on the surface is improved.

As illustrated in FIG. 8, the opening 10 is formed in a vertically long shape which is long in the longitudinal direction of the incontinence pad 1. For this reason, the body liquid easily permeates therethrough when compared to a circular opening, so that urine easily passes through the surface sheet 3 through the opening 10, and water retention to the surface sheet 3 is reduced. In addition, since the body fluid escapes while being deformed to be vertically long when urine passes through the opening 10, a diffusion direction of urine may be controlled in the longitudinal direction of the pad, diffusion in a lateral direction is suppressed, and lateral leakage rarely occurs. In the case of the spunlace, while an opening shape tends to be non-uniform, the shape of the opening 10 becomes a shape such as an approximately rectangular shape, a corner-eliminating elongated hole shape, or an elliptical shape.

With regard to dimensions of the opening 10, it is desirable that a length L1 of the incontinence pad 1 in the longitudinal direction is 1.0 to 4.0 mm, preferably 1.5 to 3.0 mm, and a length L2 of the incontinence pad 1 in the widthwise direction is 0.5 to 1.5 mm, preferably 0.5 to 1.0 mm. When a dimension of the opening 10 is less than 0.5 mm, urine hardly passes through, and it is difficult to form a clear opening due to fluffing of the fiber. When a maximum dimension of the opening 10 exceeds 4.0 mm, a liquid from the opening 10 flows back, which causes surface exposure of a constituent material of the absorber 4. In addition, it is desirable that a ratio (L1/L2) of L1 to L2 is set to 1.2 to 5.0, preferably 2.0 to 3.0. It is desirable that an area A of the opening 10 is set to 0.9 to 3.0 $mm^2$, preferably 0.9 to 2.5 $mm^2$. Further, it is desirable that the opening ratio is set to 15 to 45%, preferably 17 to 30%, more preferably 18 to 25%. The dimensions of the opening 10 may not be uniform over the whole area, and the opening 10 may be formed in an arbitrary size as long as the size falls within the above-mentioned range.

As illustrated in FIG. 8, the surface sheet 3 has a structure in which a plurality of vertical stripes 11, 11, . . . extending along the longitudinal direction of the incontinence pad 1 and formed at an interval in the widthwise direction and a plurality of horizontal stripes 12, 12, . . . extending along the widthwise direction of the incontinence pad 1, formed at an interval in the longitudinal direction, and connecting adjacent vertical stripes 11 and 11 to each other are formed by the cotton fiber, and the opening 10 is formed in a part surrounded by the vertical stripe 11 and the horizontal stripe 12.

It is desirable that a width W1 of the vertical stripe 11 is set to 0.5 to 2.5 mm, preferably 0.8 to 2.3 mm, and a width W2 of the horizontal stripe 12 is set to 0.2 to 1.6 mm, preferably 0.3 to 1.4 mm. In addition, it is desirable that a ratio (W1/W2) of the width W1 to the width W2 is set to 1.2 to 2.0, preferably 1.5 to 2.0. When the width W1 of the vertical stripe 11 is set to be larger than the width W2 of the horizontal stripe 12, liquid diffusion in the longitudinal direction of the incontinence pad 1 along the vertical stripe 11 is likely to occur.

The vertical stripe 11 is formed to have a larger fiber amount and higher density when compared to the horizontal stripe 12. In this way, only a part of the vertical stripe 11 comes into contact with the skin, a contact area with respect to the skin is reduced, and occurrence of skin trouble during wearing such as itching or rash may be suppressed after wearing for a long time. At the same time, a sticky feeling is reduced after incontinence. In addition, when urine passes through the surface sheet 3, diffusion in the longitudinal direction of the incontinence pad 1 along the vertical stripe 11 having relatively high density is likely to occur due to the capillary phenomenon of the fiber. Furthermore, since a diffusion direction of urine passing through the opening 10 and a diffusion direction of urine permeating through the surface sheet 3 coincide with each other in the longitudinal direction of the incontinence pad 1, penetration into the vertical stripe 11 of the surface sheet 3 occurs by being drawn into urine passing through the opening 10. Thus, residual liquid of the surface sheet 3 is suppressed as much as possible.

Measurement of the fiber amount can be carried out in accordance with "sieve-analysis test method of paper pulp" of JIS P8207. Further, measurement of the density can be carried in accordance with JIS P8118 "thickness and density test method".

In the surface sheet 3, a water repellent is externally added and applied at least to the section H corresponding to the excretory opening. As the water repellent, it is possible to appropriately select and use a water repellent less irritating to the skin among known water repellents such as a paraffin-based water repellent and a silicone-based water repellent, and it is more preferable to appropriately select and use oil and fat less irritating to the skin such as glyceryl stearate, stearic acid amide, zinc stearate, calcium stearate, diethanol amide stearate, or magnesium stearate. Among these materials, glyceryl stearate is particularly preferable. When a water repellent made of glyceryl stearate is used in the incontinence pad 1, a coating amount thereof is preferably set to 0.05 to 0.30 parts by weight with respect to 100 parts by weight of the fibers (in the case of double-sided coating, a total coating amount on both sides). A more preferable coating amount is 0.08 to 0.25 parts by weight. When the coating amount of the water repellent is less than 0.05 parts by weight, a water repellent effect may be insufficient in some cases. When the coating amount exceeds 0.30 parts by weight, the water repellency is excessively high, and moisture is rather difficult to permeate.

The water repellent may be applied only to the skin-contact surface or both the skin-contact surface and the surface on the absorber 4 side. However, it is desirable that at least a water absorption amount obtained from a water absorption amount test described below is 0.03 g or less, suitably 0.02 g or less.

An absorption amount of the surface sheet 3 may be obtained according to the following procedure. (1) A sample of 10 cm square is prepared, and a weight is measured (A). (2) Three paper filters of 10 cm square are stacked such that a smooth side faces upward, and the sample is set thereon. (3) 3 ml of room temperature tap water is dropped onto the set sample, and the sample is left for five minutes. (4) A weight of the sample after five minutes of leaving is measured (B). (5) The absorption amount (water retention amount) of the surface sheet 3 is obtained by (B)−(A) =absorption amount (g).

In particular, it is more preferable that the water absorbency of the surface of the surface sheet 3 on the absorber 4 side is higher than the water absorbency of the skin-contact surface. Therefore, it is desirable that the water absorbency on the skin-contact surface side (JIS L1907 Byreck method) is set to 0 mm to 5 mm, preferably 0 mm to 2 mm, and the water absorbency of the surface on the absorber 4 side (JIS L1907 Byreck method) is set to 0 mm to 10 mm, particularly preferably about 2 mm to 4 mm. Such a difference in water absorbency can be easily obtained by applying the water repellent to only the skin-contact surface of the surface sheet 3. However, the water repellent may be applied to both surfaces of the surface sheet 3. In this case, a smaller amount than that on the skin-contact surface is applied to the surface on the absorber 4 side. Even when the water repellent is applied only to the skin-contact surface of the surface sheet 3, the surface on the absorber 4 side has water repellency depending on the thickness and the basis weight. Whether the application surface of the water repellent is set to one surface or both surfaces, and a ratio of the coating amount on the both surfaces in a case in which the application surface is set to the both surfaces are appropriately selected so that liquid permeability and absorbency can be maintained in a well-balanced manner together with conditions such as the thickness, the basis weight, and the opening of the surface sheet 3.

Known methods such as transfer, spraying, brush coating, impregnation, and dipping can be appropriately used as a coating method for the water repellent. In the case of imparting a difference in water absorbency on both sides of the sheet, a coating method by transfer can be preferably used.

The water repellent is preferably applied on the entire surface from a viewpoint of manufacturing efficiency. However, it is sufficient that the water repellent is applied at least to the section H corresponding to the excretory opening, and the water repellent may be applied only to a part receiving the excreted liquid. For example, as illustrated in FIG. 9(A), a water repellent application part 40 may be provided except for both side portions in the widthwise direction. Alternatively, as illustrated in FIG. 9(B), the water repellent application part 40 may be provided only in a central part in the widthwise direction and a middle part in the front-back direction.

<Absorber 4>

The absorber 4 is capable of absorbing and retaining urine, and a superabsorbent polymer in the form of powder is dispersed and mixed in fluff-like pulp fiber and used as the absorber 4. The absorber 4 is made of only pulp fiber and the superabsorbent polymer and does not contain synthetic fiber.

Examples of the pulp fiber include a cellulose fiber such as chemical pulp or dissolved pulp obtained from wood and an artificial cellulose fiber such as rayon or acetate. Soft wood pulp having a longer fiber length than that of hardwood pulp is suitably used in terms of function and price.

It is desirable that a basis weight of the pulp fiber is set to 75 to 300 g/m$^2$, preferably 155 to 270 g/m$^2$, and it is desirable that a basis weight of the superabsorbent polymer is set to 85 to 185 g/m$^2$, preferably 100 to 165 g/m$^2$.

Examples of the superabsorbent polymer include crosslinked polyacrylate, self-crosslinked polyacrylate, a saponified product of a crosslinked product of an acrylic acid ester-vinyl acetate copolymer, a crosslinked product of an isobutylene/maleic anhydride copolymer, a crosslinked product of polysulfonate, and a partially crosslinked water-swelling polymer such as polyethylene oxide or polyacrylamide. Among these examples, acrylic acid or acrylate salt-based one which is excellent in absorption amount and absorption rate is suitable. In the manufacturing process, an absorption ratio (absorption power) and an absorption rate of the superabsorbent polymer having absorbing performance may be adjusted by adjusting crosslink density and crosslink density gradient.

It is desirable that a ratio of the pulp fiber to the superabsorbent polymer is set to pulp fiber superabsorbent polymer=70 to 30 wt %:30 to 70 wt %, preferably 62 to 45 wt %:38 to 55 wt %, more preferably 60 to 50 wt %:40 to 50 wt %.

In the incontinence pad 1, since each of the pulp fiber and the superabsorbent polymer is configured at a predetermined basis weight, and an absorber in which the pulp fiber and the superabsorbent polymer are configured at a predetermined weight ratio is used, the pulp fiber having a high absorption rate rapidly absorbs urine immediately after urination even when urine is instantaneously discharged, and then it is possible to completely prevent back flow to the surface when urine absorbed by this pulp fiber is gradually absorbed and retained in the superabsorbent polymer.

On the other hand, when the pulp fiber is more than 70 wt %, and the superabsorbent polymer is less than 30 wt %, a content ratio of the pulp fiber becomes high. Thus, the liquid retaining property of the absorber 4 is low, and back flow is likely to occur in the surface sheet 3 after urination. Meanwhile, when the pulp fiber is less than 30 wt %, and the superabsorbent polymer is more than 70 wt %, a content ratio of the superabsorbent polymer becomes high. Thus, an initial absorption rate immediately after urination is slow, transfer of urine from the surface sheet 3 to the absorber 4 is not smoothly performed, and liquid tends to remain on the surface sheet 3 immediately after urination.

In addition, urine is surely absorbed and retained in the absorber immediately after urination, and the liquid does not remain in the surface sheet. Thus, it is possible to suppress spreading of a urine diffusion range in the surface sheet.

The absorber 4 is preferably surrounded by a package sheet 5 such as crepe paper for shape retention and polymer powder retention.

<Intermediate Sheet>

In the case in which the surface sheet 3 has a large number of openings 10, an intermediate sheet 6 is preferably disposed between the surface sheet 3 and the absorber 4 to prevent the pulp, polymer, adhesive, etc. included in the absorber 4 from being exposed from the opening 10. The intermediate sheet 6 has effects of preventing back flow from the absorber 4 and softening the tactile property during wearing due to a cushion-like effect. However, the intermediate sheet 6 may or may not be disposed in a part of the surface sheet 3 in which no opening is provided. In addition, in the case of the surface sheet 3 manufactured by the above-described second method, since the second sheet 22 is laminated on the surface on the absorber 4 side, the intermediate sheet 6 may not be provided.

The intermediate sheet 6 may have a single-layer structure or a two-layer structure by being folded in a cylindrical shape. The intermediate sheet 6 may be provided over the whole of the skin-contact surface, or may be provided only in a central part in the widthwise direction and a middle part (particularly a crotch portion) in the front-back direction.

It is desirable that a material of the intermediate sheet 6 has a liquid pervious property. However, a material having hydrophilicity is particularly suitable. When the hydrophilic intermediate sheet 6 is combined with the water repellent opening surface sheet 3 of the invention, the liquid pervious property and the back flow preventing property of the surface sheet 3 are markedly improved. As such a hydrophilic material, it is possible to use a material having hydrophilicity by using a recycled fiber such as rayon or cupra and a natural fiber such as cotton, or a fiber obtained by performing a surface treatment using a hydrophilizing agent on a synthetic fiber such as an olefin-based fiber such as polyethylene or polypropylene, a polyester-based fiber, a polyamide-based fiber or a composite fiber, a copolymer, or a blend thereof, and imparting hydrophilicity thereto. Preferably, a fiber obtained by mixing polyethylene and polypropylene is used. As a fiber contained in the non-woven fabric, it is possible to use a long fiber, a short fiber, or a mixture thereof. It is desirable that the fineness is set to about 2.0 to 7.0 dtex, preferably about 4.0 to 6.0 dtex. As the intermediate sheet 6, any known non-woven fabric such as an air-through, air laid, or spunbond non-woven fabric may be used, and it is preferable to use the air-through non-woven fabric which does not lower air permeability.

In addition, in the case of the incontinence pad, as mentioned above, the incontinence pad is continuously used until the second incontinence in many cases. Thus, rather than a mere hydrophilic non-woven fabric, it is more preferable to use a strong hydrophilic or durable hydrophilic non-woven fabric obtained by spraying a strong hydrophilic and/or durable hydrophilic agent on a non-woven fabric. It is preferable that a basis weight of the strong hydrophilic agent or the durable hydrophilic agent is set to about 10 to 40 $g/m^2$, preferably about 25 $g/m^2$. A basis weight of the intermediate sheet 6 is preferably 20 to 30 $g/m^2$.

In the surface sheet 3, to prevent residual liquid of urine and make it difficult to cause skin trouble during wearing such as itching or rash, the plurality of openings 10 is formed in a region of 15% or more of the absorber length in the product length direction and 50% or more of the absorber width in the product widthwise direction preferably including the section H corresponding to the excretory opening such that the openings 10 penetrate the region from the front to the rear. Thus, the intermediate sheet 6 is disposed in a size to cover at least the entire surface of the opening formation region. Specifically, it is desirable that the intermediate sheet 6 is disposed in a size of 9% or more of the size of the absorber 4 and in the size to cover the entire surface of the opening formation region.

It is desirable that a hot melt adhesive is used for adhesion to the surface sheet 3 since heat embossing cannot be adopted. A type of hot melt adhesive is not limited. However, it is particularly desirable to use a styrene-butadiene-styrene block copolymer (SBS)-based hot melt adhesive.

The invention claimed is:

1. An absorbent article in which an absorber is interposed between a surface sheet and a back sheet,
    wherein the absorbent article is an incontinence pad having a volume sufficient to absorb 20 cc or more of urine, and
    the surface sheet is formed by applying a water repellent to a spunlace non-woven fabric containing 100 wt % of cotton fiber,
    wherein the surface sheet comprises:
    a plurality of protrusions formed along a longitudinal direction of the absorbent article and at an interval in a widthwise direction on a skin-facing surface;
    a plurality of recesses formed along the longitudinal direction of the absorbent article and between adjacent protrusions on said skin-facing surface, wherein the plurality of recesses have a smaller dimension in the widthwise direction than the plurality of protrusions; and
    a plurality of openings extending along the longitudinal direction of the surface sheet in at least a longitudinal area and penetrating through the surface sheet is formed in the plurality of recesses, wherein the surface sheet has a section that is configured to be adjacent to an excretory opening of a user when the absorbent article is worn by the user, said section defining a widthwise area and the longitudinal area, and said plurality of openings defined in at least the widthwise area;
    wherein the surface sheet is formed such that a basis weight of the plurality of recesses provided by the surface sheet is lower than an average basis weight of the plurality of protrusions and a density of the plurality of recesses provided by the surface sheet is lower than an average density of the plurality of protrusions.

2. The absorbent article according to claim 1, wherein a second sheet made of thermoplastic fiber is attached to a side of the surface sheet that faces the absorber, the surface sheet and the second sheet are joined into a combined sheet by heat sealing of the second sheet in the plurality of recesses of the surface sheet, wherein, in the combined sheet, a basis weight of the plurality of recesses is substantially the same as a basis weight of the protrusions, and a density of the plurality of recesses is higher than a density of the protrusions.

3. The absorbent article according to claim 1, wherein glyceryl stearate is used as the water repellent.

4. The absorbent article according to claim 1, wherein the surface sheet is made of absorbent cotton fiber or non-absorbent cotton fiber.

* * * * *